(12) United States Patent
Müller et al.

(10) Patent No.: US 6,407,079 B1
(45) Date of Patent: Jun. 18, 2002

(54) PHARMACEUTICAL COMPOSITIONS CONTAINING DRUGS WHICH ARE INSTABLE OR SPARINGLY SOLUBLE IN WATER AND METHODS FOR THEIR PREPARATION

(75) Inventors: Bernd W. Müller, Flintbek; Ulrich Brauns, Kiel, both of (DE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 07/264,726

(22) Filed: Oct. 31, 1988

Related U.S. Application Data

(63) Continuation of application No. 06/756,498, filed on Jul. 3, 1985, now abandoned.

(51) Int. Cl.⁷ .............................................. A61K 31/70
(52) U.S. Cl. ....................................................... 514/58
(58) Field of Search .............................. 514/58; 536/46, 536/103

(56) References Cited

U.S. PATENT DOCUMENTS

| | | | | |
|---|---|---|---|---|
| 3,459,731 A | * | 8/1969 | Gramera et al. | 260/209 |
| 4,371,673 A | * | 2/1983 | Pika | 525/426 |
| 4,383,992 A | * | 5/1983 | Lipari | 424/238 |

FOREIGN PATENT DOCUMENTS

FR        2484252        * 12/1981

* cited by examiner

*Primary Examiner*—Elli Peselev

(57) ABSTRACT

Pharmaceutical compositions comprising inclusion compounds of sparingly water-soluble or water-instable drugs with β-cyclodextrin ethers or β-cyclodextrin esters and process for the preparation thereof.

35 Claims, 2 Drawing Sheets

Figure 1:
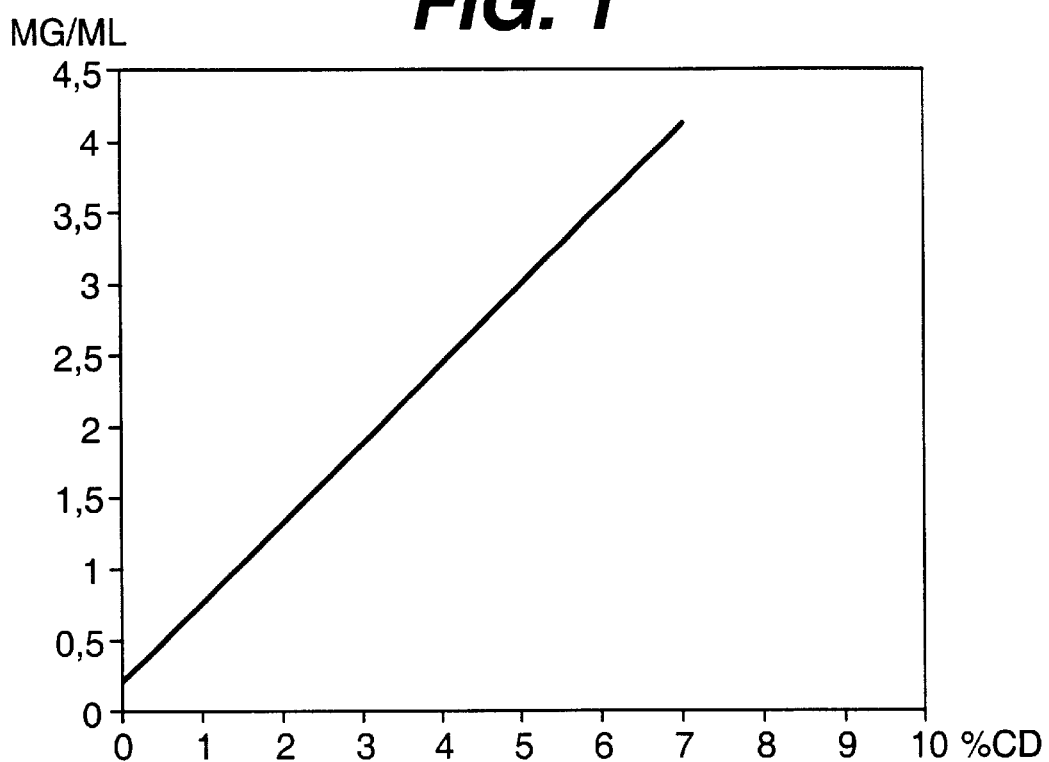

PHARMACEUTICAL COMPOSITIONS CONTAINING DRUGS WHICH ARE INSTABLE OR SPARINGLY SOLUBLE IN WATER AND METHODS FOR THEIR PREPARATION

This is a continuation of application Ser. No. 06/756,498, filed Jul. 3, 1985, now abandoned.

The invention relates to pharmaceutical compositions containing drugs which are instable or only sparingly soluble in water, and methods for their preparation. The compositions are characterized by increased water solubility and improved stability.

A large number of drugs is only poorly or sparingly soluble in water so that suitable application forms like drop solutions or injection solutions are being prepared using other polar additives like propylene glycol etc. If the drug molecule has basic or acidic groups there exists the further possibility of increasing the water solubility by salt formation. As a rule this results in decreased efficacy or impaired chemical stability. Due to the shifted distribution equilibrium the drug may penetrate the lipophilic membrane only slowly corresponding to the concentration of the non-dissociated fraction while the ionic fraction may be subject to a rapid hydrolytic decomposition.

Additional "water-like" solvents like low molecular polyethylene glycols or 1,2-propylene glycol are therefore used in the preparation of aqueous solutions of sparingly water-soluble drugs which glycols, however, cannot be considered pharmacologically inert, or the drug is solubilized using surfactants so that the drug molecules are occluded in micells. This solubilization has numerous disadvantages: The surfactant molecules used have frequently a strongly haemolytic effect and the drug needs to pass out of the micell by diffusion after the application. This results in a retard effect (compare B. W. Müller, Gelbe Reihe, Vol. X, pages 132ff (1983)).

Accordingly it may be stated that there exists no satisfactory and generally applicable method of solubilization.

For solid drugs it is also important to render the sparingly water-soluble drug water-soluble since a good solubility increases the bioavailability of the drug. It has been described that inclusion compounds, e.g. with urea or complexes of polyvinyl pyrrolidone may improve the solubility of a compound but in aqueous solution they are not stable. Such inclusion compounds are therefore at best suitable for solid application forms of drugs.

This is different when using α-, β-, and γ-cyclodextrin which can bind a drug in its ring also in aqueous solution (W. Sänger, Angewandte Chemie 92, 343 (1980)). However, it is disadvantageous that the β-cyclodextrin itself is only poorly water-soluble (1.8 g/100 ml) so that the therapeutically necessary drug concentrations are not achieved.

If a derivative is formed of the cyclodextrin its solubility and therefore the amount of dissolved drug may be considerably increased. Thus, German Offenlegungsschrift 31 18 218 discloses a solubilization method using methylated β-cyclodextrin as monomethyl derivative with 7 methyl groups and especially as dimethyl derivative with 14 methyl groups. With the 2,6-di-0-methyl derivative it is for instance possible to increase the water solubility of indometacin 20.4-fold and that of digitoxin 81.6-fold.

However, for therapeutical use the methyl derivatives of β-cyclodextrin show serious draw backs. Due to their increased lipophility they have a haemolytic effect and they further cause irritations of the mucosa and eyes. Their acute intravenous toxicity is still higher than the already considerable toxicity of the unsubstituted β-cyclodextrin. It is a further serious disadvantage for the practical application that the solubility of the dimethyl β-cyclodextrin and its complexes suffers a steep decrease at higher temperatures so that crystalline dextrin precipitates upon heating. This phenomenon makes it very difficult to sterilize the solutions at the usual temperatures of 100 to 121° C.

Quite surprisingly it has now been found that certain other β-cyclodextrin derivatives can form inclusion compounds which also considerably increase the water-solubility of sparing water-soluble and instable drugs without showing the advantages described above.

Subject of the invention are therefore novel pharmaceutical compositions comprising inclusion compounds of only sparingly water-soluble and in water instable drugs with a partially etherified β-cyclodextrin of the formula

$$(\beta\text{-CD})\text{-OR} \qquad (I),$$

in which the residues R are hydroxyalkyl groups and part of the residues R may optionally be alkyl groups, the β-cyclodextrin ether having a water-solubility of more than 1.8 g in 100 ml water.

A partially etherified β-cyclodextrin of formula I is preferably used in which the residues R are hydroxyethyl, hydroxypropyl or dihydroxypropyl groups. Optionally part of the residues R may for instance be methyl or ethyl groups; the use of partially methylated β-cyclodextrin ethers with 7 to 14 methyl groups in the β-cyclodextrin molecule, as they are known from German Offenlegungsschrift 31 18 218 do not come under the present invention. Partial ethers of β-cyclodextrin comprising only alkyl groups (methyl, ethyl) may be suitable in accordance with the invention if they have a low degree of substitution (as defined below) of 0.05 to 0.2.

β-cyclodextrin is a compound with ring structure consisting of 7 anhydro glucose units; it is also referred to as cycloheptaamylose. Each of the 7 glucose rings contains in 2-, 3-, and 6-position three hydroxy groups which may be etherified. In the partially etherified β-cyclodextrin derivatives used according to the invention only part of these hydroxy groups is etherified with hydroxyalkyl groups and optionally further with alkyl groups. When etherifying with hydroxy alkyl groups which can be carried out by reaction with the corresponding alkylene oxides, the degree of substitution is stated as molar substitution (MS), viz. in mole alkylene oxide per anhydroglucose unit, compare U.S. Pat. No. 3,459,731, column 4. In the hydroxyalkyl ethers of β-cyclodextrin used in accordance with the invention the molar substitution is between 0.05 and 10, preferably between 0.2 and 2. Particularly preferred is a molar substitution of about 0.25 to about 1.

The etherification with alkyl groups may be stated directly as degree of substitution (DS) per glucose unit which—as stated above—is 3 for complete substitution. Partially etherified β-cyclodextrins are used within the invention which comprise besides hydroxyalkyl groups also alkyl groups, especially methyl or ethyl groups, up to a degree of substitution of 0.05 to 2.0, preferably 0.2 to 1.5. Most preferably the degree of substitution with alkyl groups is between about 0.5 and about 1.2.

The molar ratio of drug to β-cyclodextrin ether is preferably about 1:6 to 4:1, especially about 1:2 to 1:1. As a rule it is preferred to use the complex forming agent in a molar excess.

Useful complex forming agents are especially the hydroxyethyl, hydroxypropyl and dihydroxypropyl ether, their corresponding mixed ethers, and further mixed ethers with methyl or ethyl groups, such as methyl-hydroxyethyl, methyl-hydroxypropyl, ethyl-hydroxyethyl and ethyl-hydroxypropyl ether of β-cyclodextrin.

The preparation of the hydroxyalkyl ethers of β-cyclodextrin may be carried out using the method of U.S. Pat. No. 3,459,731. Suitable preparation methods for β-cyclodextrin ethers may further be found in J. Sziejtli et al., Stärke 32, 165 (1980) und A. P. Croft and R. A. Bartsch, Tetrahedron 39, 1417 (1983). Mixed ethers of β-cyclodextrin can be prepared by reacting β-cyclodextrin in a basic liquid reaction medium comprising an akali metal hydroxide, water and optionally at least one organic solvent (e.g. dimethoxyethane or isopropanol) with at least two different hydroxyalkylating and optionally alkylating etherifying agents (e.g. ethylene oxide, propylene oxide, methyl or ethyl chloride).

Drugs exhibiting a significantly increased water-solubility and improved stability, respectively, after having been transferred into inclusion compounds with the above-mentioned β-cyclodextrin ethers are those having the required shape and size, i.e. which fit into the cavity of the β-cyclodextrin ring system. This includes for instance non-steroid anti-rheumatic agents, steroids, cardiac glycosides and derivatives of benzodiazepine, benzimidazole, piperidine, piperazine, imidazole or triazole.

Useful benzimidazole derivatives are thiabendazole, fuberidazole, oxibendazole, parbendazole, cambendazole, mebendazole, fenbendazole, flubendazole, albendazole, oxfendazole, nocodazole and astemisole. Suitable piperadine derivatives are fluspirilene, pimozide, penfluridole, loperamide, astemizole, ketanserine, levocabastine, cisapride, altanserine, and ritanserine. Suitable piperazine derivatives include lidoflazine, flunarizine, mianserine, oxatomide, mioflazine and cinnarizine. Examples of suitable imidazole derivatives are metronidazole, ornidazole, ipronidazole, tinidazole, isoconazole, nimorazole, burimamide, metiamide, metomidate, enilconazole, etomidate, econazole, clotrimazole, carnidazole, cimetidine, docodazole, sulconazole, parconazole, orconazole, butoconazole, triadiminole, tioconazole, valconazole, fluotrimazole, ketoconazole, oxiconazole, lombazole, bifonazole, oxmetidine, fenticonazole and tubulazole. As suitable triazole derivatives there may be mentioned virazole, itraconazole and terconazole.

Particularly valuable pharmaceutical compositions are obtained when converting etomidate, ketoconazole, tubulazole, itraconazole, levocabastine or flunarizine into a water-soluble form using the complex forming agents of the invention. Such compositions are therefore a special subject of the present invention.

The invention is further directed to a method of preparing pharmaceutical compositions of sparingly water-soluble or water-instable drugs which is characterized by dissolving the β-cyclodextrin ether in water and adding thereto the selected drug as well as optionally drying the solution of the formed inclusion compound using methods known per se. Formation of the solution may take place at temperatures between 15 and 35° C.

The drug is suitably added batchwise. The water may further comprise physiologically compatible compounds such as sodium chloride, potassium nitrate, glucose, mannitole, sorbitol, xylitol or buffers such as phosphate, acetate or citrate buffer.

Using β-cyclodextrin ethers in accordance with the invention it is possible to prepare application forms of drugs for oral, parenteral or topical application, e.g. infusion and injection solutions, drop solutions (e.g. eye drops or nasal drops), sprays, aerosols, sirups, and medical baths.

The aqueous solutions may further comprise suitable physiologically compatible preserving agents such as quarternary ammonium soaps or chlorbutanol.

For the preparation of solid formulations the solutions of the inclusion compounds are dried using conventional methods; thus the water may be evaporated in a rotation evaporator or by lyophilisation. The residue is pulverized and, optionally after addition of further inert ingredients, converted into uncoated or coated tablets, suppositories, capsules, creams or ointments.

The following examples serve to illustrate the invention which, however, is not restricted to the examples.

The phosphate buffer solution mentioned in the examples had a pH of 6.6 and the following composition:

| | |
|---|---:|
| $KH_2PO_4$ | 68.05 g |
| NaOH | 7.12 g |
| Aqua demin. ad. | 5000.0 g |

All percentages are percent by weight.

EXAMPLE 1

Figure 3:
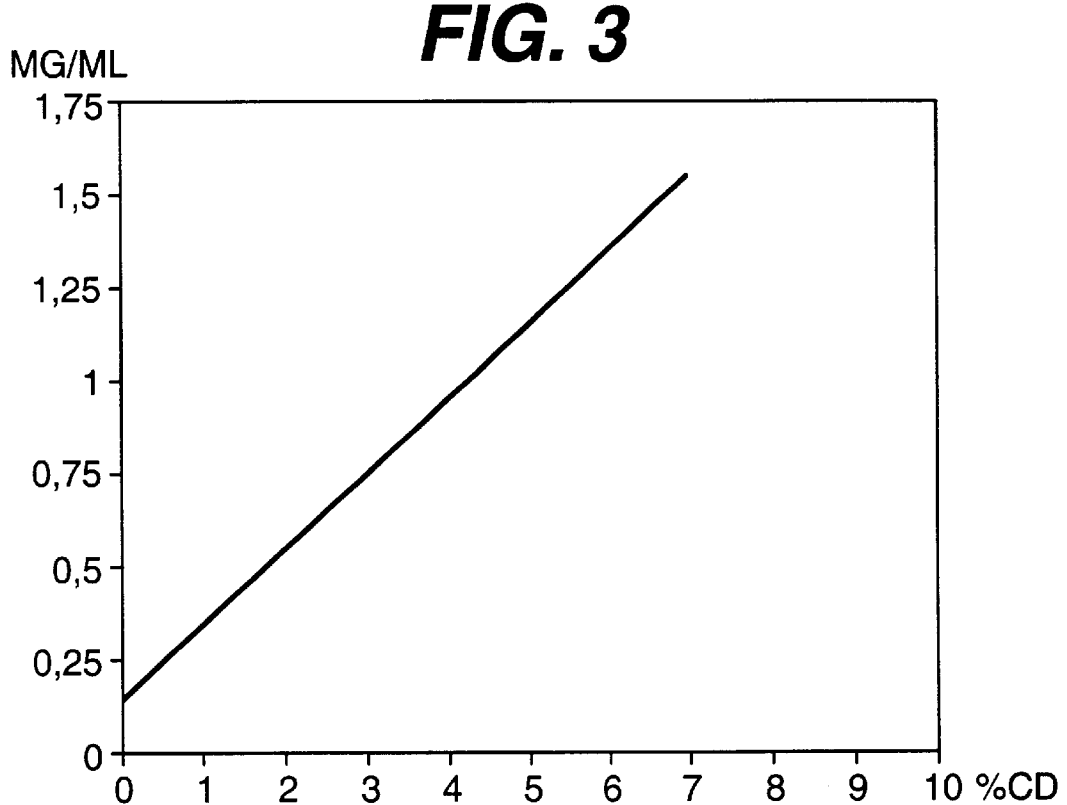
Figure 4:
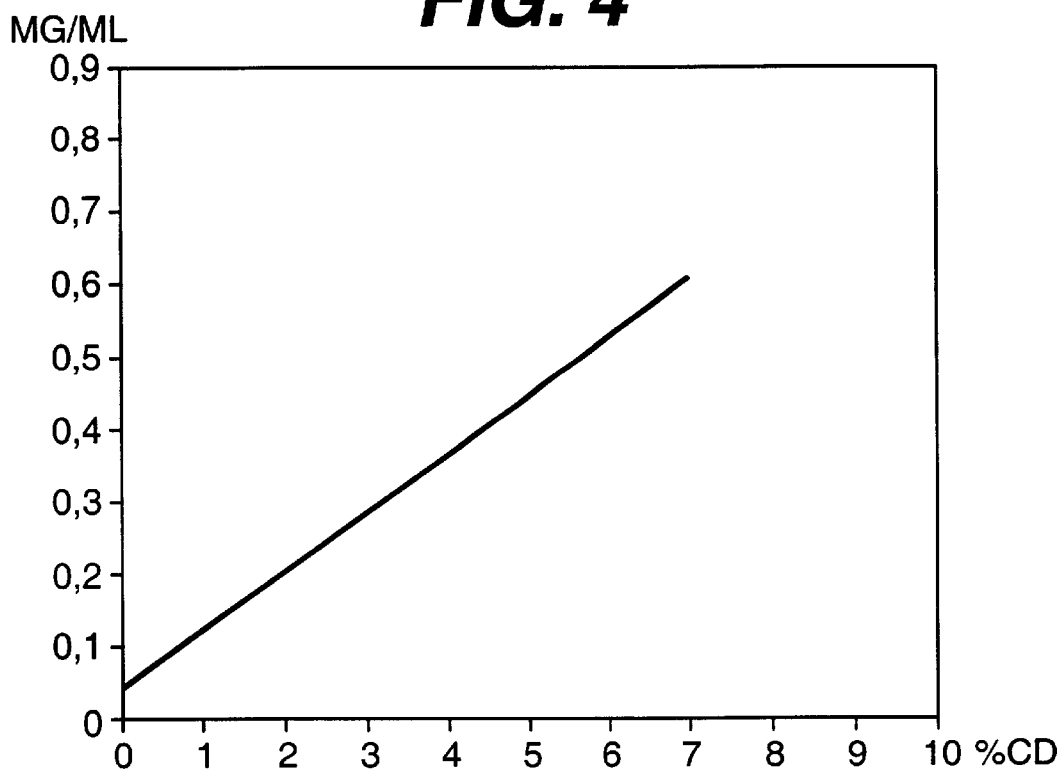

Starting from a 7% master solution of hydroxyethyl β-cyclodextrin (MS 0.43) in phosphate buffer solution a dilution series was prepared so that the complex forming agent concentration was increased in steps of 1%. 3 ml of these solutions were pipetted into 5 ml snap-top-glasses containing the drug to be tested. After shaking for 24 hours at 25° C. the solution was filtered through a membrane filter (0.22 microns) and the dissolved drug content was determined spectrophotometrically. FIGS. 1, 3 and 4 show the increase of the drug concentration in solution in relation to the concentration of the complex forming agent for indometacin (FIG. 1), piroxicam (FIG. 3) and diazepam (FIG. 4). The maximum drug concentration is limited by the saturation solubility of the cyclodextrin derivative in the buffer which in case of hydroxyethyl-β-cyclodextrin (MS 0.43) is reached at 7.2 g/100 ml.

Figure 2:
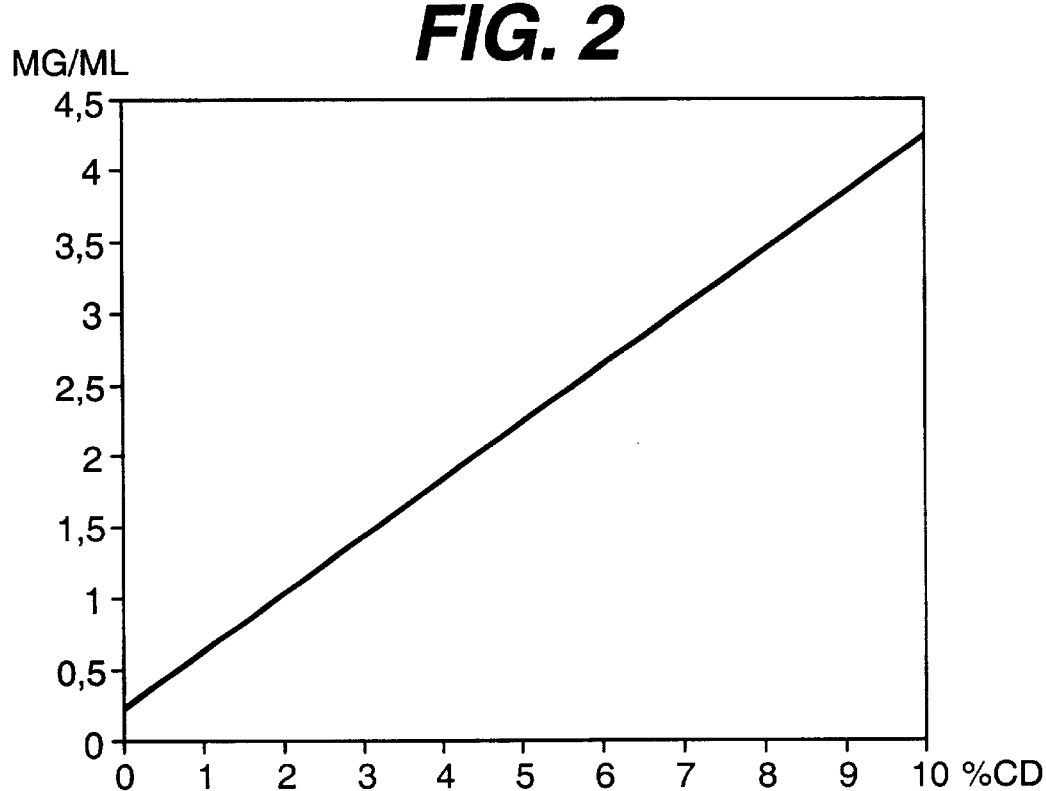

When comparing for instance the results obtained with indometacin to those given in German Offenlegungsschrift 31 18 218 for 2,6-di-O-methyl-β-cyclodextrin (FIG. 2) it will be observed that the hydroxyethyl derivative has a significantly higher complex formation constant (compare the different slopes in FIGS. 1 and 2).

EXAMPLE 2

A. The saturation solubility at 25° C. of different drugs was determined using a 10% hydroxypropyl-β-cyclodextrin solution (MS 0.35) in phosphate buffer solution under the same conditions as in example 1. The saturation solubilities $S_1$ in phosphate buffer solution and $S_2$ in phosphate buffer solution and 10% added hydroxypropyl-β-cyclodextrin are given in table 1.

TABLE 1

| Drugs | $S_1$ (mg/ml) | $S_2$ (mg/ml) | Ratio $S_1:S_2$ |
|---|---|---|---|
| Indometacine | 0.19 | 5.72 | 1:30.1 |
| Digitoxine | 0.002 | 1.685 | 1:842.5 |
| Progesterone | 0.0071 | 7.69 | 1:1083.0 |
| Dexamethasone | 0.083 | 14.28 | 1:172.0 |
| Hydrocortisone | 0.36 | 21.58 | 1:59.9 |
| Diazepame | 0.032 | 0.94 | 1:29.4 |

B. The solubility of drugs in a 4% aqueous solution of hydroxypropyl-methyl-β-cyclodextrin (DS 0.96; MS 0.43) was determined in a similar manner. The results obtained are summarized in the following table 2 in which the ratio R of the saturation solubility in water or at the stated pH, respectively, with an without addition of β-cyclodextrin derivative is stated for each drug. The solutions prepared according to the invention were further found to be significantly more stable when compared with aqueous solutions.

TABLE 2

| Drug | | R |
|---|---|---|
| Itraconazole | at pH 5 | 96 |
| | at pH 2.5 | 75 |
| Flunarizine | | 18 |
| Levocabastine | at pH 9.5 | 81 |
| | at pH 7.4 | 8 |
| Ketoconazole | | 85 |
| Flubendazole | | 30 |
| Tubulazole | | 43 |
| Cisapride | | 3 |
| Loperamide | | 62 |
| Etomidate | | 8.5 |
| Cinnarizine | at pH 5 | 28 |
| | at pH 3 | 12 |

EXAMPLE 3

In 10 ml phosphate buffer solution 0.7 g hydroxyethyl-β-cyclodextrin (MS 0.43) were dissolved together with 0.04 g indometacin at 25° C. until a clear solution was formed. This solution was filtered through a membrane filter (0.22 microns) and filled under laminar flow into a pre-sterilized injection bottle which was stored at 21° C. (B). In a parallel test a saturated indometacin solution in a phosphate buffer solution (0.21 mg/ml) was stored under the same conditions (A). The drug concentrations determined by high pressure liquid chromatography are given in table 3. The great improved stability of the composition according to the invention is apparent.

TABLE 3

| Storing time | Indometacin content (%) | |
|---|---|---|
| in weeks | A | B |
| 0 | 100.1 | 99.7 |
| 2 | 91.2 | 99.9 |
| 4 | 79.1 | 98.1 |
| 6 | 69.8 | 98.6 |
| 8 | 64.8 | 98.4 |

EXAMPLE 4

Injectable Formulation 0.35 g hydroxypropyl-β-cyclodextrin (MS 0.35) were dissolved in 5 ml of physiological sodium chloride solution and warmed to about 35° C. whereafter 3 mg diazepam were added. After storing for a short time a clear solution was obtained which was filled into an ampule after filtration through a membrane filter (0.45 microns).

EXAMPLE 5

Tablet

In 100 ml water 7 g hydroxyethyl-β-cyclodextrin (MS 0.43) and 0.5 g medroxyprogesterone acetate were dissolved. The water was then evaporated in a rotation evaporator The residue (75 mg) was powdered and after addition of 366 mg calcium hydrogen phosphate.2H$_2$O, 60 mg corn starch, 120 mg cellulose powder (microcrystalline), 4.2 mg highly dispersed silica (AEROSIL® 200) and 4.8 mg magnesium stearate tablets with a weight of 630.0 mg and comprising 5 mg drug per unit dose were made. The dissolution rate of the medroxyprogesterone acetate from this formulation is 21 times higher when compared to a tablet comprising the same inert ingredients without addition of the β-cyclodextrin ether.

EXAMPLE 6

5 g hydroxyethyl-β-cyclodextrin (MS 0,43) and 14 mg vitamin A-acetate were dissolved with stirring in 100 ml water or sugar solution (5% aqueous solution) within 2.5 hours under a nitrogen atmosphere. After filtration through a membrane filter (0.45 microns) the solution was filled into ampules and sterilized or filled into dropper bottles with addition of 0.4% chlor butanol as preserving agent.

EXAMPLE 7

5 or 7.5 g hydroxyethyl β-cyclodextrin (MS 0.43) and 0.5 or 0.75 g Lidocaine were dissolved in 100 ml of physiological sodium chloride solution at 30° C. (B). Injection solutions, eye droplets and solutions for topical use were prepared therefrom as described in example 6. When comparing the anaethesic effect of these solutions in animal tests with an aqueous lidocain HCl solution (A) one observes an extension of the duration of the effect by 300%. Test: rats, injection of 0.1 ml into the tail root in the vicinity of the right or left nerve fillaments and electrical irritation. The test results are summarized in table 4.

TABLE 4

| Drug concentration | Duration of effect (min) | | Extension |
|---|---|---|---|
| (%) | A | B | (%) |
| 0.5 | 56 | 163 | 291 |
| 0.75 | 118 | 390 | 330 |

EXAMPLE 8

6 mg dexamethasone and 100 mg hydroxyethyl-β-cyclodextrin (MS 0.43) were dissolved in 5 ml water, sterilized by filtration through a membrane filter (0.22 microns) and packed into an aerosol container allowing to dispense 0.1 ml per dose.

EXAMPLE 9

The acute intravenous toxicity of some β-cyclodextrins was tested on rats with the following results. It was surprisingly found that the toxicity of the derivatives used according to the invention is lower by an entire order of magnitude.

TABLE 5

| LD$_{50}$ in rats (i.v.) in mg/kg bodyweight | |
|---|---|
| β-cyclodextrin | 453 |
| dimethyl-β-cyclodextrin (DS 2.0) | 200–207 |
| hydroxypropyl-methyl-β-cyclodextrin (DS 0.96; MS 0.43) | >2000* |

*a higher dose has not been tested. In mice the value was >4000 mg/kg.

The haemolytic effect of the methylether according to German Offenlegungsschrift 31 18 218 was compared to that of an ether used according to the invention. To this end 100 μl of a physiological sodium chloride solution with a cyclodextrin content of 10%, 800 μl of a buffer (400 mg MOPS, 36 mg $Na_2HPO_4.2H_2O$, 1,6 g NaCl in 200 ml $H_2O$) and 100 μl of a suspension of human red blood cells (three times washed with sodium chloride solution) were mixed for 30 minutes at 37° C. Thereafter the mixture was centrifuged and the optical density was determined at 540 nm.

Controls:

a) 100 μl sodium chloride solution+buffer+0% haemolysis b) 900 μl water→100% haemolysis The results obtained are summarized in the following table 6 in which the concentrations are stated at which 50% and 100% haemolysis occurred.

TABLE 6

| Substance | $C_{50}\%$ | $C_{100}\%$ |
|---|---|---|
| Dimethyl-β-CD (DS 2.0) | 0.33% | 0.5% |
| Methyl-β-CD (DS 1.79) | 0.53 | 0.8% |
| Hydroxypropyl-methyl-β-CD (DS 0.96; MS 0.43%) | 1.5% | 4% |

The results show that the haemolytic effect of the hydroxypropylmethyl ether is about 5 to 8 times weaker than that of the dimethyl ether according to the prior art. Animal tests have further shown that the hydroxyalkyl ethers do not cause irritation of the mucosa and eyes in contrast to the methyl ethers.

We claim:

1. Pharmaceutical composition comprising an inclusion compound of (i) a drug capable of fitting into the cavity of the cyclodextrin ring system which is instable or only sparingly soluble in water with (ii) a partially etherified β-cyclodextrin of the formula:

(β-CD)—OR (I)

wherein the residues R are hydroxyalkyl groups and part of said residues R may optionally be alkyl groups, the βcyclodextrin ether having a water solubility of greater than 1.8 g in 100 ml water, wherein said composition has considerably increased water solubility and stability relative to said drugs, with very low toxicity.

2. Composition according to claim 1 wherein said residues R are hydroxyethyl, hydroxypropyl, dihydroxypropyl, methyl or ethyl groups.

3. Composition according to claim 2, wherein said partially etherified β-cyclodextrin of formula I has a molar substitution by hydroxyalkyl groups of 0.05 to 10 and a degree of substitution by alkyl groups of 0 to 2.0.

4. Composition according to claim 1, wherein said drug and said β-cyclodextrin ether are in a molar ratio of 1:6 to 4:1.

5. Composition according to claim 1, wherein said drug is a non-steroid anti-rheumatic agent, a steroid, a cardiac glycoside or derivatives of benzodiazepine, benzimidazole, piperidine, piperazine, imidazole or triazole.

6. Composition according to claim 1, wherein said drug is etomidate.

7. Composition according to claim 1, wherein said drug is ketoconazole.

8. Composition according to claim 1, wherein said drug is itraconazole.

9. Composition according to claim 1, wherein said drug is levocabastine.

10. Composition according to claim 1, wherein said drug is flunarizine.

11. Composition according to claim 1, wherein said drug is tubulazole.

12. Pharmaceutical composition comprising an inclusion compound of (i) a drug which is instable or only sparingly soluble in water and which is capable of fitting into the cavity of the β-cyclodextrin ring system and (ii) a β-cyclodextrin derivative of the formula:

(β-CD)—OR wherein β-CD represents β-cyclodextrin and the residue(s) R is selected from hydroxyethyl, hydroxypropyl, dihydroxypropyl, methyl, and ethyl or mixtures thereof; provided that;

(a) the molar substitution by hydroxyethyl, hydroxypropyl, and dihydroxypropyl is from 0.05 to 10, and (b) the degree of substitution by methyl and ethyl is from 0 to 2.0 and (c) the molar ratio of said drug to said β-cyclodextrin derivative is from 1:6 to 4:1, and (d) the water solubility of said β-cyclodextrin derivative is greater than 1.8 g in 100 ml of water.

13. The composition of claim 12 wherein said molar substitution is from 0.2 to 2.

14. The composition of claim 12 wherein said molar substitution is from about 0.25 to about 1.

15. The composition of claim 12 wherein said molar ratio is from 0.2 to 2.

16. The composition of claim 12 wherein said molar ratio is from about 0.5 to about 1.2.

17. The composition of claim 12 wherein said drug is selected from etomidate, ketoconazole, tubulazole, itraconazole, levacabastine, and flunarizine.

18. A method of producing a stabilizing amorphous complex of a drug and mixture of beta-cyclodextrin derivatives comprising the steps of:

(1) dissolving the intrinsically amorphous mixture of beta-cyclodextrin derivatives which are water soluble and capable of forming inclusion complexes with drugs in water, and (2) solubilizing sparingly water-soluble drugs into the aqueous media to form a solution and form a solubilized drug/cyclodextrin complex.

19. A method of claim 18 wherein the cyclodextrins used are substituted by the following substituents: hydroxyalkyl.

20. A method of claim 18 wherein the drug is progesterone.

21. A composition of matter which contains a water-soluble amorphous complex of beta-cyclodextrin derivatives and a drug.

22. A composition of claim 21 wherein the drug is progesterone.

23. A composition of matter for use in the process of claim 18 containing a mixture of substituted beta-cyclodextrin ethers in amorphous form.

24. A composition of matter in solid form comprising progesterone as an inclusion complex with hydroxypropyl-beta-cyclodextrin adapted for administration by the oral route.

25. The composition of claim 12 wherein the residue R is selected from hydroxyethyl with a molar substitution of from 0.2 to 2, and methyl and ethyl with a degree of substitution of 0 to 2.0.

26. The composition of claim 12 wherein the residue R is selected from hydroxypropyl with a molar substitution of from 0.2 to 2, and methyl and ethyl with a degree of substitution of 0 to 2.0.

27. Pharmaceutical composition comprising an inclusion compound of (i) a drug capable of fitting into the cavity of the β-cyclodextrin ring system which is instable or only sparingly soluble in water and (ii) a partially etherified β-cyclodextrin derivative of the formula:

(β-CD)—OR wherein β-CD represents β-cyclodextrin and the residue R is a hydroxyalkyl group and the β-cyclodextrin has a molar substitution by hydroxyalkyl of about 0.25 to about 1.

28. Composition according to claim 27 wherein the hydroxyalkyl group is selected from hydroxyethyl, hydroxypropyl and dihydroxypropyl.

29. Composition according to claim 27 wherein the hydroxyalkyl group is hydroxyethyl and the molar ratio of said drug to said β-cyclodextrin derivative is from about 1:6 to 4:1.

30. Composition according to claim 27 wherein the hydroxypropyl group is hydroxyethyl and the molar ratio of said drug to said β-cyclodextrin derivative is from about 1:6 to 4:1.

31. Pharmaceutical composition comprising an inclusion compound of (i) a drug capable of fitting into the cavity of the β-cyclodextrin ring system which is instable or only sparingly soluble in water and (ii) a partially etherified β-cyclodextrin derivative of the formula:

(β-CD)—OR wherein β-CD represents β-cyclodextrin and the residues R are in part hydroxyalkyl groups and in part alkyl groups, said alkyl groups being present up to a degree of substitution between about 0.05 to 2.

32. Composition according to claim 31 wherein the alkyl groups hydroxyalkyl groups are selected from hydroxyethyl, hydroxypropyl and dihydroxypropyl having a molar substitution of about 0.2 to 2, and the alkyl groups are methyl or ethyl being present up to a degree of substitution between about 0.5 and 1.2.

33. Composition according to claim 32 wherein the hydroxyalkyl group is hydroxyethyl having a molar substitution of about 0.25 to about 1.

34. Composition according to claim 32 wherein the hydroxyalkyl group is hydroxpropyl having a molar substitution of about 0.25 to about 1.

35. Composition according to claim 32 wherein the ratio of said drug to said β-cyclodextrin derivative is from about 1:6 to 4:1.

* * * * *

(12) EX PARTE REEXAMINATION CERTIFICATE (10336th)
United States Patent
Müller et al.

(10) Number: US 6,407,079 C1
(45) Certificate Issued: Oct. 16, 2014

(54) PHARMACEUTICAL COMPOSITIONS CONTAINING DRUGS WHICH ARE INSTABLE OR SPARINGLY SOLUBLE IN WATER AND METHODS FOR THE PREPARATION

(75) Inventors: Bernd W. Müller, Flintbek (DE); Ulrich Brauns, Kiel (DE)

(73) Assignee: Janssen Pharmaceutica N.V., Beerse (BE)

Reexamination Request:
No. 90/010,886, Mar. 4, 2010

Reexamination Certificate for:
Patent No.: 6,407,079
Issued: Jun. 18, 2002
Appl. No.: 07/264,726
Filed: Oct. 31, 1988

Related U.S. Application Data

(63) Continuation of application No. 06/756,498, filed on Jul. 3, 1985, now abandoned.

(30) Foreign Application Priority Data

Dec. 21, 1983 (DE) .................... P3346123

(51) Int. Cl.
*A61K 9/00* (2006.01)
*A61K 9/20* (2006.01)
*A61K 31/451* (2006.01)
*A61K 31/495* (2006.01)
*A61K 31/496* (2006.01)
*A61K 31/4164* (2006.01)
*A61K 31/4174* (2006.01)
*A61K 47/02* (2006.01)
*A61K 47/48* (2006.01)
*B82Y 5/00* (2011.01)

(52) U.S. Cl.
CPC ........... *A61K 9/0019* (2013.01); *A61K 31/4174* (2013.01); *A61K 31/495* (2013.01); *A61K 9/2054* (2013.01); *A61K 31/451* (2013.01); *B82Y 5/00* (2013.01); *A61K 47/48969* (2013.01); *A61K 47/02* (2013.01); *A61K 9/0048* (2013.01); *A61K 31/496* (2013.01)
USPC ........................................................ 514/58

(58) Field of Classification Search
None
See application file for complete search history.

(56) References Cited

To view the complete listing of prior art documents cited during the proceeding for Reexamination Control Number 90/010,886, please refer to the USPTO's public Patent Application Information Retrieval (PAIR) system under the Display References tab.

*Primary Examiner* — Dwayne Jones

(57) ABSTRACT

Pharmaceutical compositions comprising inclusion compounds of sparingly water-soluble or water-instable drugs with β-cyclodextrin ethers or β-cyclodextrin esters and process for the preparation thereof.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-17, 24-29, 31-33 and 35 is confirmed.

Claim 21 is cancelled.

Claims 18, 22, 30 and 34 are determined to be patentable as amended.

Claims 19, 20 and 23, dependent on an amended claim, are determined to be patentable.

New claims 36-40 are added and determined to be patentable.

18. A method of producing [a stabilizing amorphous complex of a drug and mixture of beta-cyclodextrin derivatives] *the inclusion compound of claim 1* comprising the steps of:

(1) dissolving the [intrinsically amorphous mixture of beta-cyclodextrin derivatives which are water soluble and capable of forming inclusion complexes with drugs] *partially etherified β-cyclodextrin* in water, and (2) solubilizing sparingly water-soluble drugs into the aqueous media to form a solution and form a solubilized drug/cyclodextrin complex.

22. A composition of claim [21] *1* wherein the drug is progesterone.

30. Composition according to claim 27 wherein the [hydroxypropyl] *hydroxyalkyl* group is hydroxyethyl and the molar ratio of said drug to said β-cyclodextrin derivative is from about 1:6 to 4:1.

34. Composition according to claim 32 wherein the hydroxyalkyl group is [hydroxpropyl] *hydroxypropyl* having a molar substitution of about 0.25 to about 1.

*36. Composition according to claim 1, wherein said drug is a derivative of benzodiazepine, benzimidazole, piperidine, piperazine, imidazole or triazole.*

*37. Composition according to claim 12, wherein said drug is a derivative of benzodiazepine, benzimidazole, piperidine, piperazine, imidazole or triazole.*

*38. Composition according to claim 27, wherein said drug is a derivative of benzodiazepine, benzimidazole, piperidine, piperazine, imidazole or triazole.*

*39. Composition according to claim 31, wherein said drug is a derivative of benzodiazepine, benzimidazole, piperidine, piperazine, imidazole or triazole.*

*40. A method according to claim 18, wherein said drug is a derivative of benzodiazepine, benzimidazole, piperidine, piperazine, imidazole or triazole.*

\* \* \* \* \*